United States Patent
Launay et al.

(10) Patent No.: US 6,834,096 B2
(45) Date of Patent: Dec. 21, 2004

(54) APPARATUS AND METHOD FOR PROVIDING A THREE-DIMENSIONAL RADIOGRAPHIC IMAGE OF AN OBJECT

(75) Inventors: Laurent Launay, Saint Remy les Chevreuse (FR); Sébastien Gicquel, Cambridge, MA (US); Yves Trousset, Palaiseau (FR)

(73) Assignee: GE Medical Systems Global Technology Company LLC, Waukesha, NJ (US)

( * ) Notice: Subject to any disclaimer, the term of this patent is extended or adjusted under 35 U.S.C. 154(b) by 0 days.

(21) Appl. No.: 10/116,625

(22) Filed: Apr. 4, 2002

(65) Prior Publication Data

US 2002/0196894 A1 Dec. 26, 2002

(30) Foreign Application Priority Data

Apr. 9, 2001 (FR) .......................................... 01 04771

(51) Int. Cl.[7] ................................................. A61B 6/00
(52) U.S. Cl. ......................... 378/8; 378/95; 378/98.12; 600/431
(58) Field of Search ...................... 378/4, 8, 95, 98.11, 378/98.12; 382/130, 131; 600/431

(56) References Cited

U.S. PATENT DOCUMENTS

| | | | | |
|---|---|---|---|---|
| 4,593,355 A | | 6/1986 | Chase ........................ 382/131 |
| 4,878,169 A | | 10/1989 | Tonner et al. .............. 382/131 |
| 4,903,202 A | * | 2/1990 | Crawford .................... 382/131 |
| 4,943,987 A | | 7/1990 | Asahina et al. ............ 378/98.5 |
| 5,029,586 A | * | 7/1991 | Honda ........................ 600/425 |
| 5,570,404 A | | 10/1996 | Liang et al. ................... 378/8 |
| 5,602,891 A | * | 2/1997 | Pearlman ..................... 378/62 |
| 5,802,133 A | * | 9/1998 | Kawai et al. .................. 378/4 |
| 5,920,319 A | | 7/1999 | Vining et al. ............... 345/420 |
| 5,978,439 A | * | 11/1999 | Koppe et al. .................. 378/8 |
| 6,324,243 B1 | * | 11/2001 | Edic et al. ..................... 378/4 |
| 6,366,635 B1 | * | 4/2002 | Op De Beek et al. .......... 378/4 |
| 6,404,843 B1 | * | 6/2002 | Vaillant ......................... 378/8 |
| 6,426,994 B1 | * | 7/2002 | Van Vaals ................ 378/98.12 |
| 6,574,500 B2 | * | 6/2003 | Keren ......................... 600/431 |

OTHER PUBLICATIONS

Feldkamp et al, "Practical Cone—Beam Algorithm", J.Opt. Soc. Am. v. 1, No. 6 Jun. 1984, pp. 612–619.

* cited by examiner

*Primary Examiner*—Edward J. Glick
*Assistant Examiner*—Allen C. Ho
(74) *Attorney, Agent, or Firm*—Jay L. Chaskin; Cantor Colburn LLP

(57) ABSTRACT

An apparatus and method comprises an acquisition of a first series of projected two-dimensional mask images of the object obtained for different positions of a camera around the object; an acquisition of a second series of opacified projected two-dimensional images of the object obtained at the same positions of the camera around the object; a phase of elaboration of a third series of subtracted projected two-dimensional images respectively obtained from the first and second series of images; a reconstruction of a three-dimensional subtracted image from the third series of images and from an analytical algorithm of image reconstruction; a reconstruction of a three-dimensional mask image from the first series of images and from an analytical algorithm of image reconstruction; a phase of identification of defects in the three-dimensional mask image; and elimination of the corresponding voxels in the three-dimensional subtracted image.

9 Claims, 3 Drawing Sheets

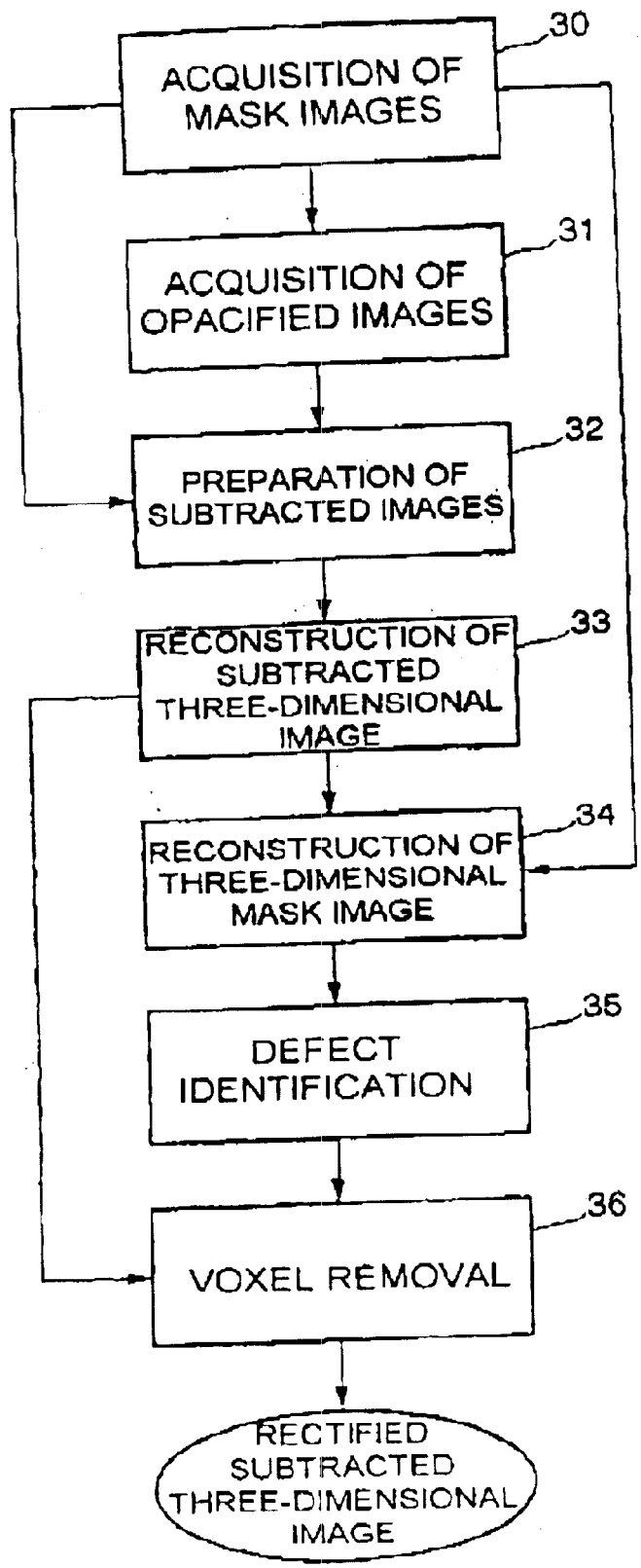

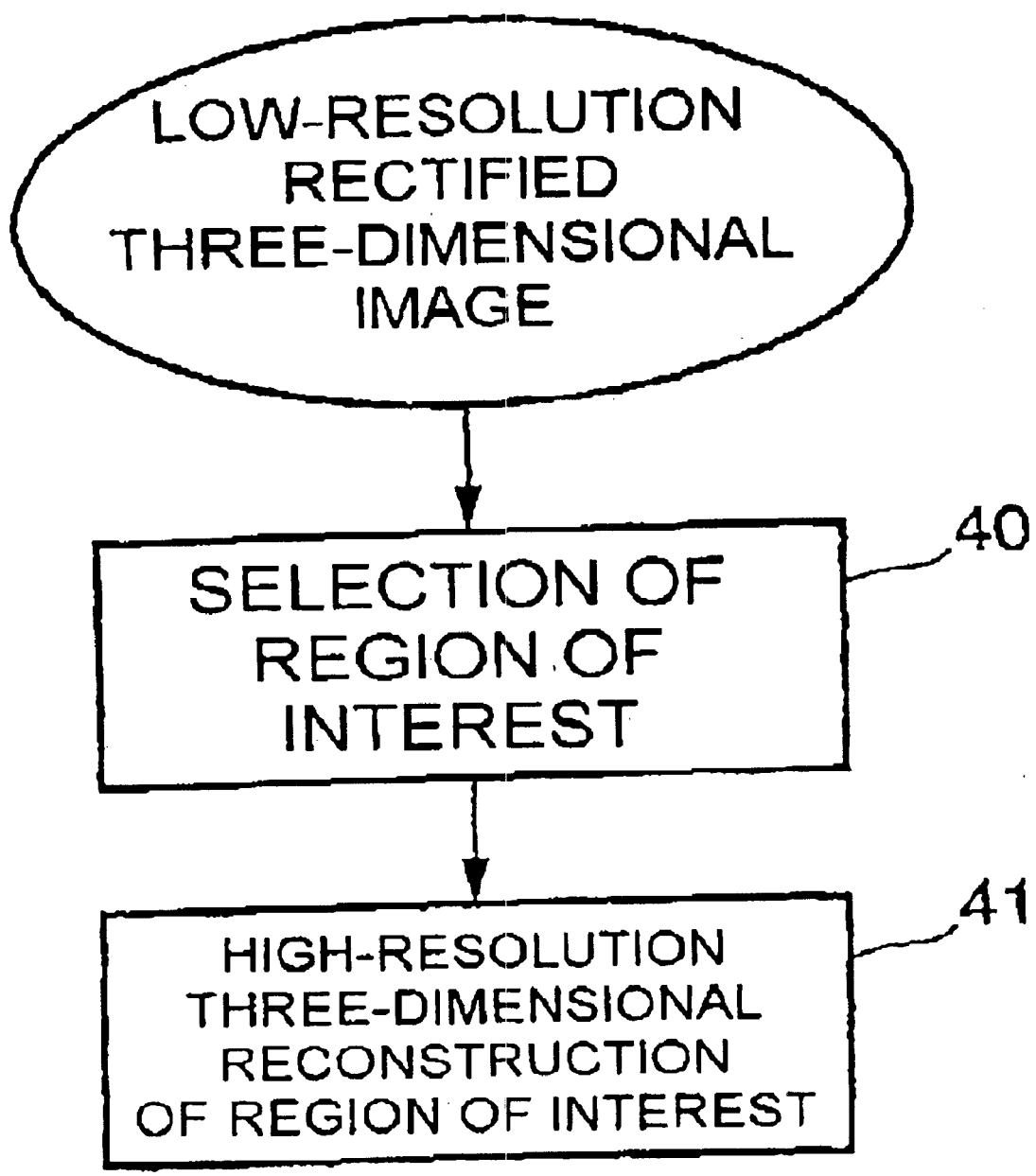

APPARATUS AND METHOD FOR PROVIDING A THREE-DIMENSIONAL RADIOGRAPHIC IMAGE OF AN OBJECT

CROSS-REFERENCE TO RELATED APPLICATIONS

This application claims the benefit of a priority under 35 USC 119 to French Patent Application No. 0104771 filed Apr. 9, 2001, the entire contents of which are incorporated by reference.

BACKGROUND OF THE INVENTION

This invention is directed to the reconstruction of a three-dimensional image of an object from a set of two-dimensional projected images of the object, obtained for different positions of a means for acquiring an image, for example, by a camera, around the object.

The invention is of interest to the field of medical diagnostic imaging, in which reconstruction of the internal structures of an object, such as a patient, under examination is undertaken. In particular, the invention is applicable to the reconstruction of angiographic images, that is, obtaining images of vascular systems opacified by injection of a contrast medium.

In the field of medical diagnostic imaging, two-dimensional projected images of the object, for example, a patient's abdomen, are generally obtained by rotation of an X-ray camera around the object. In an abdominal imaging application, peristalsis is known to cause defects in the reconstructed three-dimensional images. Those defects are due to the displacement of gas bubbles between the acquisition of so-called mask images, that is, in which no contrast medium has been injected, and the acquisition of opacified images. In other words, this produces white and black regions in the subtracted images. This phenomenon is particularly disturbing for three-dimensional reconstructions from subtracted projected images, because six to ten seconds can elapse between acquisition of the series of mask images and acquisition of the corresponding series of opacified images. The first negative effect of those defects is to disturb display of the reconstructed image by reason of their superposition on the vessels in three-dimensional images. As a result, the user removes the superposition manually by using, for example, an electronic scalpel. Another undesirable effect is produced when a multiresolution approach is used for reconstruction of the three-dimensional image. In that case, the signal comprises a large quantity of voxels and can lead to the suppression of some small vessels of the region which is reconstructed at high resolution.

BRIEF DESCRIPTION OF THE INVENTION

The invention is directed to a reduction, preferably automatically, and even a total suppression of such defects in three-dimensional image reconstruction, particularly in abdominal angiographic images.

An embodiment of the invention is a method reconstruction of a three-dimensional radiographic image of an object, comprising:

(a) acquisition of a first series of projected two-dimensional mask images of the object obtained for different positions of a means for image acquisition, e.g. a camera, around the object;

(b) acquisition of a second series of opacified projected two-dimensional images of the object obtained at the same positions of the camera around the object;

(c) elaborating a third series of subtracted projected two-dimensional images respectively obtained from the first and second series of images;

(d) reconstruction of a subtracted three-dimensional image from the third series of images and from an analytical algorithm of image reconstruction;

(e) reconstruction of a three-dimensional mask image from a first series of images and from an analytical algorithm of image reconstruction;

(f) identification of defects in the three-dimensional mask image; and (g) elimination of the corresponding voxels in the three-dimensional subtracted image.

According to one embodiment of the invention, the elimination of voxels entails resetting the intensity value.

According to another embodiment of the invention, the two three-dimensional image reconstructions are carried out at a first resolution, for example, a low resolution. A region of interest is then selected in the three-dimensional subtracted image and a new three-dimensional reconstruction is made of the region of interest alone, with a second resolution higher than the first resolution.

The invention is also directed to a radiographic apparatus for reconstructing a three-dimensional radiographic image of an object, comprising:

(a) means for acquiring images, such as a camera capable of rotating around the object;

(b) means for acquiring a first series of projected two-dimensional mask images of the object obtained for different positions of the camera rotating around the object;

(c) means for acquiring a second series of opacified projected two-dimensional images of the object obtained at the same positions of the camera around the object;

(d) means for elaborating a third series of subtracted projected two-dimensional images respectively obtained from the first and second series of images;

(e) means for reconstructing a subtracted three-dimensional image from the third series of images and from an analytical algorithm of image reconstruction;

(f) means for reconstruction of a three-dimensional mask image from the first series of images and from an analytical algorithm of image reconstruction;

(g) means for identifying defects in the three-dimensional mask image; and (h) means for post-treatment for eliminating the corresponding voxels in the subtracted three-dimensional image.

BRIEF DESCRIPTION OF THE DRAWING

Other advantages and characteristics of the invention will appear from a detailed description of a nonlimitative embodiment and attached drawings in which:

FIGS. 3 and 4 schematically illustrate flow charts relating to an application of an embodiment of the method.

DETAILED DESCRIPTION OF THE INVENTION

Figure 1:
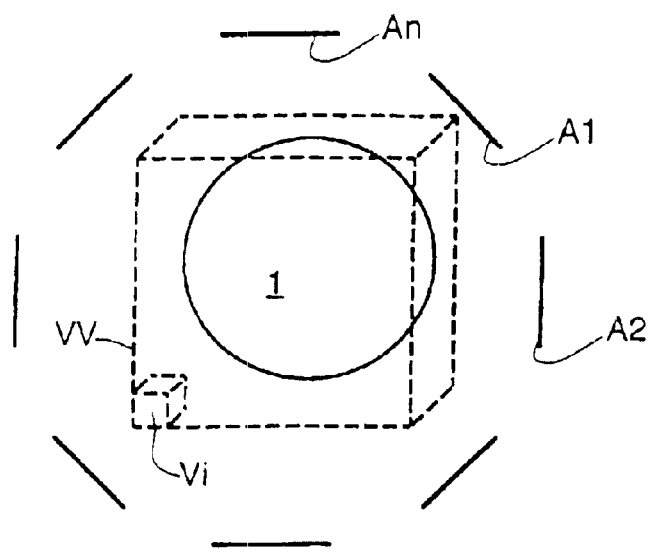
FIG. 1 schematically illustrates a set of two-dimensional projected images around an object.
Figure 2:
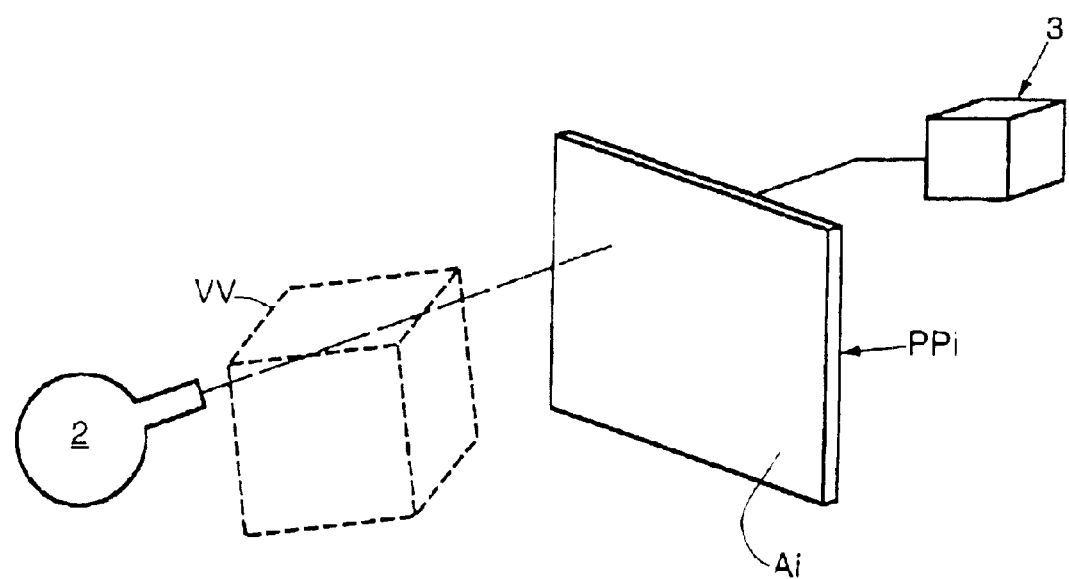
FIG. 2 illustrates in greater detail the acquisition of one of the two-dimensional projected images.

FIGS. 1 and 2 illustrate an imaging apparatus to obtain a set of two-dimensional acquired images Al–An. The acquired images are, for example. produced by a 180° rotation of a means for providing radiation, for example, X-ray source 2, around an object, e.g., a patient's abdomen 1. As is conventional in angiography, each acquired image Ai is a subtracted image which is, for example, obtained by a standard technique of logarithmic subtraction of two X-rays taken at the same angle of incidence before and after an injection of a contrast medium in the vascular system, the three-dimensional image of which it is desired to reconstruct.

A virtual volume VV that can contain the patient's abdomen is subdivided into voxels Vi. Each acquired image Ai is obtained from a means for detection, comprising, typically a two-dimensional radiation detector, for example, of the luminance amplifier type used in radiology, placed opposite the X-ray source in a plane indicated as a projection plane PPi. The different projection planes are obtained by the different angular positions of the detector in rotation around the object, e.g., patient's head or abdomen. The detector is connected to a means for processing 3 comprising means for sampling connected to a microprocessor incorporating as software in its associated program memory an analytical algorithm of image reconstruction and, in general, all of the functional means making possible the use of the method according to an embodiment of the invention.

In general, when the movement of gas bubbles occurs only between the end of acquisition of the mask images and the start of the opacified images, the gas bubbles are visible in the reconstructed mask and opacified images. Since those gas bubbles are made of air, they are characterized by a weaker intensity than the intensity of all the other structures. The disturbing signal in the subtracted reconstructed image is, consequently, due to the subtraction between a region composed of tissues in one image and composed of air in the other. The signal comprises of two parts: (1) a negative part which corresponds to the presence of tissues in the mask image and of air in the opacified image. That negative part is not disturbing in the subtracted reconstructed image because the final volume is thresholded and only the positive intensities are retained: and (2) a positive part which corresponds to the presence of air in the mask image and of tissues in the opacified image. That part is disturbing because the intensity of the subtracted image representing the bubble is comparable to the intensity of the subtracted signal representing the vessels. On the basis of that observation, the general principle of an embodiment of the invention is as follows:

(1) carrying out a standard reconstruction of a three-dimensional image;

(2) carrying out a supplementary reconstruction of a three-dimensional mask image by solely using the two-dimensional projected mask images;

(3) identifying, on that reconstructed mask image, the defects (e.g., gas bubbles) by any technique known to the expert, for example, a thresholding or any other segmentation technique; and (4) removing from the subtracted three-dimensional image reconstructed the voxels contained in the region of defect previously identified, or else resetting their intensity.

It is then possible to eliminate all the defects of the three-dimensional reconstructed subtracted image. But, in some actual cases, the movement of the gas bubbles can also occur during acquisition of the mask images and during acquisition of the opacified images. This will then result in the subsistence of some defects in the subtracted three-dimensional image reconstructed. However, there will be a notable reduction of the number of defects.

FIG. 3 illustrates an embodiment of the method where in stage 30 there is an acquisition of two-dimensional projected mask images and in stage 31 an acquisition of two-dimensional projected opacified images.

In stage 32, subtracted images are elaborated from mask images and from opacified images. A reconstruction is then undertaken of the subtracted two-dimensional images (stage 33) from the subtracted two-dimensional images elaborated in stage 32 and from an analytical algorithm of image reconstruction. A known algorithm is described, for example in "Practical cone-beam algorithm" by L. A. Feldkamp, L. C. Davis and J. W. Kress. Journal Optical Society of America, Vol. 1, No. 6. June 1984. In general, Feldkamp's analytical algorithm mainly comprises a filtering stage and a back projection stage. A three-dimensional mask image reconstruction is likewise undertaken (stage 34) from the two-dimensional mask images acquired in stage 30 and from an analytical algorithm of image reconstruction which can also be Feldkamp's algorithm.

The defect, i.e., gas bubbles are identified (stage 35) in the reconstructed three-dimensional image, for example, by using a thresholding or other segmentation technique. Thresholding can be adaptive or not.

The voxels corresponding to the defects (stage 36) are then eliminated in the subtracted three-dimensional image reconstructed in stage 33 so as to obtain a rectified subtracted three-dimensional image.

In practice, such an application can be penalizing from the standpoint of computing time, because it requires two reconstructions, one of which is a non-subtracted reconstruction (reconstruction of the three-dimensional mask image).

Also, according to one particularly advantageous embodiment, it is preferable to use a multiresolution approach, such as that briefly described in FIG. 4. From the rectified three-dimensional image, which has been obtained from two low-resolution reconstructions, a region of interest is selected (stage 40), for example, a region surrounding a vessel. A new three-dimensional reconstruction (stage 41) of that region of interest is made from the subtracted two-dimensional images, but this time using a high resolution. With such a multiresolution approach, the cost in terms of computing time is reduced by approximately 75%, which renders it completely compatible with use in a medical field.

Various modifications in structure and/or steps an/or function may be made by one skilled in the art without departing form the scope and extent of the invention as recited in the claims.

What is claimed is:

1. A method of providing a three-dimensional radiographic image of an object, comprising:

acquiring a first series of projected two-dimensional mask images of the object obtained for different positions around the object;

acquiring a second series of opacified projected two-dimensional images of the object obtained at the same positions around the object;

elaborating a third series of subtracted projected two-dimensional images respectively obtained from the first and second series of images;

reconstruction of a three-dimensional subtracted image from the third series of images and from an analytical algorithm of image reconstruction;

reconstruction of a three-dimensional mask image from a first series of images and from an analytical algorithm of image reconstruction;

identification of defects in the three-dimensional mask image; and elimination of corresponding voxels in the three-dimensional subtracted image.

2. The method according to claim 1, wherein the elimination of voxels entails resetting their intensity value.

3. The method according to claim 1, wherein the two three-dimensional image reconstructions:

are carried out at a first resolution, in that a region of interest is selected in the three-dimensional subtracted image; and a new three-dimensional reconstruction is made of the region of interest alone, with a second resolution higher than the first resolution.

4. The method according to claim 2, wherein the two three-dimensional image reconstructions:

are carried out at a first resolution, in that a region of interest is selected (40) in the three-dimensional subtracted image; and a new three-dimensional reconstruction is made of the region of interest alone, with a second resolution higher than the first resolution.

5. An apparatus for three-dimensional radiographic imaging of an object, comprising:

means for image acquisition rotating around the object;

means for acquiring a first series of projected two-dimensional mask images of the object obtained for different positions around the object, and a second series of opacified projected two-dimensional images of the object, obtained at the same positions around the object, means for elaborating a third series of subtracted projected two-dimensional images respectively obtained from the first and second series of images;

means for reconstructing a subtracted three-dimensional image from the third series of images and from an analytical algorithm of image reconstruction, and a three-dimensional mask image from the first series of images and from an analytical algorithm of image reconstruction;

means for identifying defects in the three-dimensional mask image; and means for eliminating the corresponding voxels in the subtracted three-dimensional image.

6. The apparatus according to claim 5, wherein the means for eliminating comprises means for resetting the values of the voxels to be eliminated.

7. The apparatus according to claim 5, wherein the:

means for reconstruction carries out the two three-dimensional image reconstructions at a first resolution; and apparatus comprises means for selecting a region of interest in the subtracted three-dimensional image, whereby the means for reconstruction carries out a new three-dimensional reconstruction of the region of interest alone, with a second resolution higher than the first resolution.

8. The apparatus according to claim 6, wherein the:

means for reconstruction carries out the two three-dimensional image reconstructions at a first resolution, and apparatus comprises means for selecting a region of interest in the subtracted three-dimensional image, whereby the means for reconstruction carries out a new three-dimensional reconstruction of the region of interest alone, with a second resolution higher than the first resolution.

9. A method for providing a radiographic image comprising:

carrying out a known first reconstruction of a three-dimensional image;

carrying out a supplementary reconstruction of a three-dimensional mask image by subtraction using solely two-dimensional mask images;

wherein the two three-dimensional image reconstructions are carried out at a first resolution, in that a region of interest is selected in the three-dimensional subtracted image; and a new three-dimensional reconstruction is made of the region of interest alone, with a second resolution higher than the first resolution;

identifying defects in the reconstructed mask image; and removing from the reconstructed subtracted three-dimensional image voxels contained in a region of the identified defect or resetting the intensity value of the voxels.

* * * * *